(12) United States Patent
Shirai et al.

(10) Patent No.: US 7,312,177 B2
(45) Date of Patent: Dec. 25, 2007

(54) THERMOSENSITIVE RECORDING MATERIALS

(75) Inventors: Ayako Shirai, Yokohama (JP); Yoshiyuki Takahashi, Tokyo (JP)

(73) Assignee: Oji Paper Co., Ltd., Tokyo (JP)

( * ) Notice: Subject to any disclaimer, the term of this patent is extended or adjusted under 35 U.S.C. 154(b) by 443 days.

(21) Appl. No.: 10/933,391

(22) Filed: Sep. 3, 2004

(65) Prior Publication Data

US 2005/0054528 A1     Mar. 10, 2005

(30) Foreign Application Priority Data

Sep. 8, 2003   (JP)  ............................. 2003-315885

(51) Int. Cl.
  *B41M 5/30*  (2006.01)
(52) U.S. Cl. ........................ 503/216; 560/12
(58) Field of Classification Search ................. None
  See application file for complete search history.

(56) References Cited

U.S. PATENT DOCUMENTS

| | | | |
|---|---|---|---|
| 5,246,906 A | 9/1993 | Takahashi et al. | |
| 5,256,618 A | 10/1993 | Takahashi et al. | |
| 5,801,288 A | 9/1998 | Fujii et al. | |
| 6,486,094 B1 | 11/2002 | Shirai et al. | |
| 2003/0040434 A1 | 2/2003 | Fujita et al. | ................. 503/216 |

FOREIGN PATENT DOCUMENTS

EP       1044824       10/2000

JP       2000-355578    12/2000

OTHER PUBLICATIONS

European Patent Office communication for corresponding European Patent Application No. 04255417.0-1211-dated Dec. 17, 2004.

*Primary Examiner*—Bruce H. Hess
(74) *Attorney, Agent, or Firm*—Kratz, Quintos & Hanson, LLP

(57) ABSTRACT

A thermosensitive recording material comprising a substrate sheet and a thermosensitive colored image-forming layer formed on at least one surface of the substrate sheet and comprising at least one colorless or light-colored dye precursor and a color-developing agent reactive with the dye precursor upon heating to thereby develop a color, wherein the color-developing agent comprises at least one compound of the formula (I):

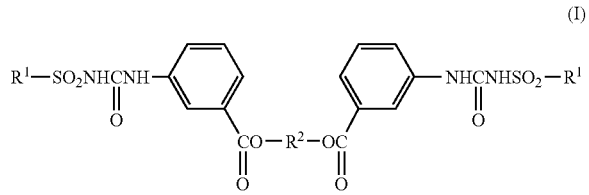

(wherein $R^1$ represents a member selected from the group consisting of unsubstituted aromatic hydrocarbon groups and substituted aromatic hydrocarbon groups with at least one substituent selected from the group consisting of a methyl group and a chlorine atom, and $R^2$ represents a divalent organic group).

5 Claims, No Drawings

THERMOSENSITIVE RECORDING MATERIALS

BACKGROUND OF THE INVENTION

1. Field of the Invention

The present invention relates to thermosensitive recording materials for forming colored images upon heating. More particularly, the present invention relates to thermosensitive recording materials having a high whiteness, an excellent colored image-retaining stability, due to which the color-developed images are not erased, and a high recording sensitivity. The thermosensitive recording materials of the present invention exhibit a good storage property over a long time, have a high environmental resistance such as a high humidity resistance, a high oil resistance, and a high plasticizer resistance of the recorded images, and have a high recording sensitivity and whiteness. Thus the thermosensitive recording materials of the present invention are usable for image-recording sheets, cash-dispenser sheets, ticket cards, commuting ticket cards, labels, for example, POS labels, cards, for example, prepaid cards, and pass cards.

2. Prior Art

Generally, a thermosensitive recording material comprises a substrate comprising a paper sheet, a synthetic paper sheet or a plastic film, and a thermosensitive colored image-forming layer formed on the substrate and comprising, as principal components, a color-forming component, for example, an electron-donative leuco dye and a color-developing component comprising an organic acid substance, for example, an electron-acceptive phenol compound. The above-mentioned two components react with each other upon heating to form colored images. This type of thermosensitive recording material is disclosed in Japanese Examined Patent Publication (Kokoku) No. 43-4160, Japanese Examined Patent Publication (Kokoku) No. 45-14039, and Japanese Examined Patent Publication (Kokoku) No. 48-27736, and is employed in practice.

The thermosensitive recording material is compact, cheap and is easy to maintain, and thus is used in a broad range of practical applications, for example, outputs of computers, facsimiles, automatic ticket vending machines, printers for scientific and measurement equipments, printer for CRT medical measurements and the like. However, in the conventional thermosensitive recording materials having a substrate sheet coated with a thermosensitive colored image-forming layer comprising a color-forming dye component, a color-developing component and a binder as the active components, the color-forming reaction is reversible and thus it is known that the colored images is erased with the lapse of time. The color-erasure is accelerated when the images are exposed to light, a high humidity atmosphere, or a high temperature atmosphere. The color-erasure is further promoted by immersing in water for long period or by contacting with an oil, for example, salad oil, or with a plasticizer, to such an extent that the images cannot be read or noted.

On the other hand, it is also known that dye type thermosensitive recording materials undergo a color forming reaction upon heating, so if held in a high temperature, high humidity environment, will spontaneously form color (hereafter, so called "spontaneous color formation") leading to a deterioration of the contrast and difficulty in discriminating the recorded image. Further, thermosensitive recording type parking lot tickets and highway tickets left in motor vehicles in hot summer weather and thermosensitive type POS labels heated by microwave ovens along with food they are attached to in supermarkets or convenience stores suffer from serious spontaneous color formation, making it almost impossible to read the recorded images.

Much technology has been disclosed for suppressing the color-erasure phenomenon using a color-forming system containing a dye including, as a principal component, a normally colorless or light colored lactone cyclic compound. For example, in one attempt, a phenol compound-containing antioxidant is contained in the thermosensitive colored image-forming layer as disclosed in Japanese Unexamined Patent Publication (Kokai) No. 60-78782, Japanese Unexamined Patent Publication (Kokai) No. 59-167292, Japanese Unexamined Patent Publication (Kokai) No. 59-114096, and Japanese Unexamined Patent Publication (Kokai) No. 59-93387; in another attempt, a protective layer is formed from a hydrophobic polymer emulsion on the thermosensitive colored image-forming layer as disclosed in Japanese Unexamined Patent Publication (Kokai) No. 56-146796; in still another attempt, the thermosensitive colored image-forming layer is coated with an intermediate layer formed from an emulsion of a water-soluble polymeric compound or a hydrophobic polymeric compound, and the intermediate layer is coated by a surface layer formed from a oily lacquer containing, as a resin component, a hydrophobic polymeric compound, as disclosed in Japanese Unexamined Patent Publication (Kokai) No. 58-199189; in still another attempt, a phenol compound-containing color developing agent is employed in combination with an epoxy compound as disclosed in Japanese Unexamined Patent Publication (Kokai) No. 62-164579; and in further another attempt, a metal salt of a specific salicylic acid derivative is employed as a color-developing agent as disclosed in Japanese Unexamined Patent Publication (Kokai) No. 62-169681. However, none of these is deemed to exhibit much of an effect of improvement or else, while some degree of improvement is seen, a long time is required for it to be manifested or the effect does not last long or otherwise is not satisfactory. Further, sometimes the improving procedure results in problems such as spontaneous color formation due to high heat or high humidity, a drop in recording sensitivity, etc. A more practical proposal has therefore been awaited for a long time.

As a completely different strategy from the above, technology has been disclosed using a sulfonylurea compound for the color developing agent instead of the conventional organic acid compounds like phenol (see Japanese Unexamined Patent Publication (Kokai) No. 5-147357, p. 2 and Japanese Unexamined Patent Publication (Kokai) No. 5-32601, pp. 2 to 4). The proposal of using a sulfonylurea compound as the color developing agent is extremely epoch-making. It not only creates novel color-forming functional groups, but also succeeds in completely suppressing the phenomenon of erasure of the recorded image of thermosensitive recording materials not only under various environment conditions such as high temperatures and high humidities, but also in contact with oil or plasticizers—which had been considered impossible in the past. Thermosensitive recording materials with an extremely high storage stability of recorded images were, therefore, accomplished.

However, due to the striking improvement in the storage stability of the recorded images of thermosensitive recording materials by sulfonylurea color developing agents, a strong demand has arisen for early improvement of the other problem in thermosensitive recording materials, that is, the spontaneous color formation when held under a high temperature or high humidity and the consequent deterioration of contrast and difficulty in discerning the recorded images. That is, while the proposal for use of sulfonylurea compounds for color developing agents has been effective in improving the storage stability of recorded images, suppression of the spontaneous color formation occurring under more severe environmental conditions which are sought at the present time has not yet necessarily been achieved.

Further, while sulfonylurea based color developing agents similar in chemical structure to the present invention (for example, see Japanese Unexamined Patent Publication (Kokai) No. 2000-355578, pp. 2 to 8) which are effective in improving the storage stability of recorded images have been proposed, the suppression of the spontaneous color formation under harsh environmental conditions which are currently sought cannot be said to be sufficient.

Thermosensitive recording materials form colors due to heating as part of their inherent system, so spontaneous color formation under high temperature environments is unavoidable, but improvements in color developing agents and sensitizers have made it possible to keep this to a lower level (for example, see Japanese Unexamined Patent Publication (Kokai) No. 6-1069, p. 2). In recent years, however, performance has been sought from thermosensitive paper enabling resistance to spontaneous color formation, and consequently, good contract and legibility even when, for example, thermosensitive recording type-parking or highway tickets using it are left in cars in hot summer weather or when thermosensitive recording type POS labels are heated by microwave ovens along with the food they are attached to in supermarkets or convenience stores. A great turning point has been reached in thermosensitive recording materials.

As one proposal to meet this demand, there is the method of using compounds with relatively high molecular weights for the color developing agent. This proposal, however, also results in a low stability of recorded images and is not sufficient for practical use (for example, see Japanese Unexamined Patent Publication (Kokai) No. 8-333329, p. 2).

In this way, no thermosensitive recording materials offering both storage stability of the recorded images and suppression of spontaneous color formation under harsher environments, and further having both practical and sufficient basic performance have yet been proposed.

DISCLOSURE OF THE INVENTION

An object of the present invention is to provide a thermosensitive recording material having a high whiteness and resistance to spontaneous color formation in environmental resistance tests, in particular under high temperature conditions as envisioned inside motor vehicles in hot summer weather and in heating in microwave ovens, free from erasure of the recorded images, and superior in oil resistance, plasticizer resistance and other facets of long term storability of the colored-image.

Another object of the present invention is to provide a thermosensitive recording material not only useful for highway and other road tickets and thermosensitive recording type traveller's tickets and parking lot tickets for ticket-vending machines, but also for coupon book tickets and commuter passes which must have a high storage stability and labels for POS barcode systems adhered to packaging of food wrapped in polyvinyl chloride films and unavoidably in contact with oils or plasticizers.

The above-mentioned objects can be attained by the thermosensitive recording materials of the present invention, that is:

(1) A thermosensitive recording material comprising a substrate sheet and a thermosensitive colored image-forming layer formed on at least one surface of the substrate sheet and comprising at least one colorless or light-colored dye precursor and a color-developing agent reactive with the dye precursor upon heating to thereby develop a color, wherein the color-developing agent comprises at least one compound of the formula (I):

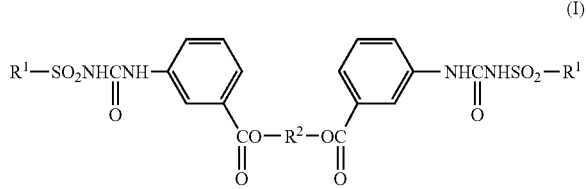

wherein $R^1$ represents a member selected from the group consisting of unsubstituted aromatic hydrocarbon groups and substituted aromatic hydrocarbon groups with at least one substituent selected from the group consisting of a methyl group and a chlorine atom, and $R^2$ represents a divalent organic group.

(2) The thermosensitive recording material as according to (1), wherein in the formula (I), the divalent organic group represented by $R^2$ is selected from the group consisting of —$(CH_2)_m$— groups, and —$(CH_2CH_2O)_n$—$CH_2CH_2$— groups, wherein m represents an integer of 1 to 30, and n represents an integer of 1 to 20.

(3) 1,5-(3-oxopentylene)bis(3-(3'-(p-toluenesulfonyl)ureido)benzoate) of the following chemical formula (II):

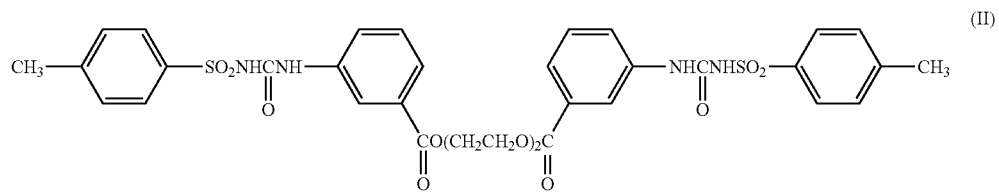

(4) 1,5-pentamethylene bis(3-(3'-(p-toluenesulfonyl)ureido)benzoate) of the following chemical formula (III):

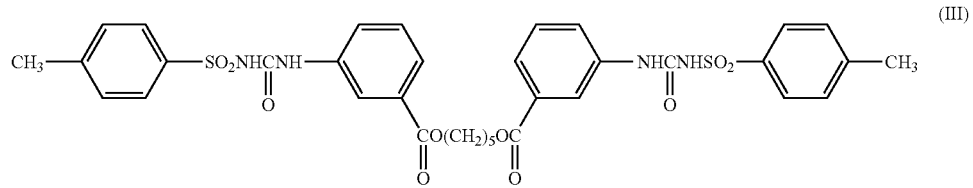

(5) 1,6-hexamethylene bis(3-(3'-(p-toluenesulfonyl)ureido)benzoate) of the following chemical formula (IV):

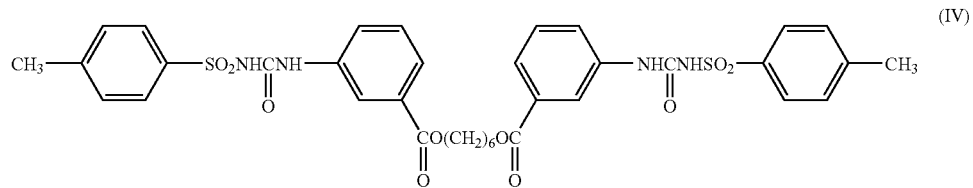

The thermosensitive recording material of the present invention uses an aromatic hydrocarbon compound of the general formula (I) as a color-developing agent in the thermosensitive colored-image forming layer, so exhibits a high whiteness and a high colored-image forming performance. Further, it is substantially free from spontaneous color formation and exhibits high colored-image storability even if left in high temperature and high humidity environments, in particular harsh environments such as in cars in hot summer weather or during heating in microwave ovens. The thermosensitive recording material of the present invention using the aromatic hydrocarbon compound of general formula (I) as a color-developing agent in the thermosensitive colored-image forming layer exhibits an extremely high colored-image storability even in contact with a plasticizer or PVC film.

BEST MODE FOR CARRYING OUT THE INVENTION

The compounds of the formula (I) used in the thermosensitive colored image-forming layer of the present invention serve as color-developing agents. Namely, although the compounds of the formula (I) have no acid functional group, for example, phenolic hydroxyl group or carboxyl group, they exhibit a strong color-developing property to basic leuco dye. The strong color-developing property is assumed to be due to a phenomenon in which the urea groups in the compound of the formulae (I) are activated by the sulfonyl group located adjacent to the urea group.

In the formula (I), the group represented by $R^1$ is selected from the group consisting of unsubstituted aromatic hydrocarbon groups and substituted aromatic hydrocarbon groups with at least one substituent selected from the group consisting of a methyl group and a chlorine atom. Particularly, $R^1$ is preferably selected from a phenyl group, a 2-naphthyl group, a p-tolyl group, an o-tolyl group, a m-tolyl group and a p-chlorophenyl group, or the like.

In the formula (I), the group represented by $R^2$ is not specifically limited to specific groups, as long as the $R^2$ group is a divalent organic group. Preferably, the group represented by $R^2$ is a member selected from the following group.

(a) Divalent groups corresponding to those of aliphatic or cycloaliphatic hydrocarbons, from each of which structures two hydrogen atoms are excluded, particularly —$(CH_2)_m$— groups in which m represents an integer of 1 to 30.

Preferably, the group (a) includes methylene, dimethylene, trimethylene, tetramethylene, pentamethylene, hexamethylene, or those having substituent on their side chain, such as 1-methyl-1,3-trimethylene, 2,3-dimethyl-1,4-tetramethylene, 1,4-cyclohexylene, 1,4-cyclohexane dimethylene groups.

(b) Divalent groups having chemical structures corresponding to those of aliphatic or cycloaliphatic hydrocarbons partially substituted by hetero atoms, from each of which structures two hydrogen atoms are excluded, particularly —(CH$_2$CH$_2$O)$_n$—CH$_2$CH$_2$— group, wherein n represents an integer of 1 to 20.

Preferably, the group (b) includes 1,5-(3-oxapentylene), 1,5-(3-thiopentylene), 1,8-(3,6-dioxaoctylene), 2,5-(1-oxacyclohexylene), 1-oxacyclohexane-2,5-dimethylene groups.

(c) Divalent groups having chemical structure corresponding to those of alkyl-substituted aromatic hydrocarbon groups or heteroalkyl-substituted aromatic hydrocarbon groups, in each of which structures, two hydrogen atoms are excluded, from the alkyl group or the hetero atom-substituted group.

Preferably, the group (c) include an α,α'-(p-xylylene) group, an α,α'-(m-xylylene) group, a β,β'-(1,4-di(dimethylene)benzene) group, and a γ,γ'-(1,4-di(dimethylene)benzene) group.

Specific compounds of the color-developing agent according to the present invention include the following: as examples of compounds of the formula (I), methylene bis(3-(3'-(p-toluenesulfonyl)ureido)benzoate),
methylene bis(3-(3'-(m-toluenesulfonyl)ureido)benzoate),
methylene bis(3-(3'-(o-toluenesulfonyl)ureido)benzoate),
1,2-dimethylene bis(3-(3'-(p-toluenesulfonyl)ureido)benzoate),
1,2-dimethylene bis(3-(3'-(m-toluenesulfonyl)ureido)benzoate),
1,2-dimethylene bis(3-(3'-(o-toluenesulfonyl)ureido)benzoate),
1,3-trimethylene bis(3-(3'-(p-toluenesulfonyl)ureido)benzoate),
1,3-trimethylene bis(3-(3'-(o-toluenesulfonyl)ureido)benzoate),
1,3-trimethylene bis(3-(3'-(m-toluenesulfonyl)ureido)benzoate),
1,4-tetramethylene bis(3-(3'-(p-toluenesulfonyl)ureido)benzoate),
1,4-tetramethylene bis(3-(3'-(o-toluenesulfonyl)ureido)benzoate),
1,4-tetramethylene bis(3-(3'-(m-toluenesulfonyl)ureido)benzoate),
1,5-pentamethylene bis(3-(3'-(p-toluenesulfonyl)ureido)benzoate),
1,5-pentamethylene bis(3-(3'-(m-toluenesulfonyl)ureido)benzoate),
1,5-pentamethylene bis(3-(3'-(o-toluenesulfonyl)ureido)benzoate),
1,6-hexamethylene bis(3-(3'-(p-toluenesulfonyl)ureido)benzoate),
1,6-hexamethylene bis(3-(3'-(m-toluenesulfonyl)ureido)benzoate),
1,6-hexamethylene bis(3-(3'-(o-toluenesulfonyl)ureido)benzoate),
1,7-heptamethylene bis(3-(3'-(p-toluenesulfonyl)ureido)benzoate),
1,7-heptamethylene bis(3-(3'-(m-toluenesulfonyl)ureido)benzoate),
1,7-heptamethylene bis(3-(3'-(o-toluenesulfonyl)ureido)benzoate),
1,8-octamethylene bis(3-(3'-(p-toluenesulfonyl)ureido)benzoate),
1,8-octamethylene bis(3-(3'-(m-toluenesulfonyl)ureido)benzoate),
1,8-octamethylene bis(3-(3'-(o-toluenesulfonyl)ureido)benzoate),
1,9-nonamethylene bis(3-(3'-(p-toluenesulfonyl)ureido)benzoate),
1,9-nonamethylene bis(3-(3'-(m-toluenesulfonyl)ureido)benzoate),
1,9-nonamethylene bis(3-(3'-(o-toluenesulfonyl)ureido)benzoate),
1-methylethylene bis(3-(3'-(p-toluenesulfonyl)ureido)benzoate),
1-methylethylene bis(3-(3'-(o-toluenesulfonyl)ureido)benzoate),
1-methylethylene bis(3-(3'-(m-toluenesulfonyl)ureido)benzoate),
1,5-(3-oxopentylene)bis(3-(3'-(p-toluenesulfonyl)ureido)benzoate),
1,5-(3-oxopentylene)bis(3-(3'-(m-toluenesulfonyl)ureido)benzoate),
1,5-(3-oxopentylene)bis(3-(3'-(o-toluenesulfonyl)ureido)benzoate),
1,8-(3,6-dioxaoctylene) bis(3-(3'-(p-toluenesulfonyl)ureido)benzoate),
1,8-(3,6-dioxaoctylene) bis(3-(3'-(m-toluenesulfonyl)ureido)benzoate),
1,8-(3,6-dioxaoctylene) bis(3-(3'-(o-toluenesulfonyl)ureido)benzoate),
α,α'-(1,4-cyclohexane dimethylene) bis(3-(3'-(p-toluenesulfonyl)ureido)benzoate),
α,α'-(1,4-cyclohexane dimethylene) bis(3-(3'-(o-toluenesulfonyl)ureido)benzoate),
α,α'-(p-xylylene) bis(3-(3'-(p-toluenesulfonyl)ureido)benzoate),
α,α'-(p-xylylene) bis(3-(3'-(m-toluenesulfonyl)ureido)benzoate).

Among these, from the viewpoint of exhibiting a superior color developing performance and exhibiting also a particularly superior image preservation, 1,5-(3-oxopentylene) bis(3-(3'-(p-toluenesulfonyl)ureido)benzoate), 1,5-pentamethylene bis(3-(3'-(p-toluenesulfonyl)ureido)benzoate) and 1,6-hexamethylene bis(3-(3'-(p-toluenesulfonyl)ureido)benzoate) are particularly preferred. These compounds may be used alone or in mixtures of two or more types.

The leuco dyes usable as dye-precursors in the present invention may be selected from conventional leuco dyes, for example, triphenylmethane dyes, fluoran dyes, and diphenylmethane dyes. For example, one or more type may be selected from 3-(4-diethylamino-2-ethoxyphenyl)-3-(1-ethyl-2-methylindol-3-yl)-4-azaphthalide, crystal violet lactone, 3-(N-ethyl-N-isopentylamino)-6-methyl-7-anilinofluoran, 3-diethylamino-6-methyl-7-anilinofluoran, 3-diethylamino-6-methyl-7-(o, p-dimethylanilino)fluoran, 3-(N-ethyl-N-p-toluidino)-6-methyl-7-anilinofluoran, 3-pyrrolidino-6-methyl-7-anilinofluoran, 3-dibutylamino-6-methyl-7-anilinofluoran, 3-(N-cyclohexyl-N-methylamino)-6-methyl-7-anilinofluoran, 3-diethylamino-7-(o-chloroanilino)fluoran, 3-diethylamino-7-(o-chloroanilino)fluoran, 3-dibutylamino-7-(m-trifluoromethylanilino)fluoran, 3-diethylamino-6-methyl-7-chlorofluoran, 3-diethylamino-6-methylfluoran, 3-cyclohexyl amino-6-chlorofluoran, 3-(N-ethyl-N-hexylamino)-6-methyl-7-(p-chloroanilino)fluoran, and 3-(N,N-dipentylamino)-6-methyl-7-anilinofluoran.

In the present invention, to an extent not impairing the desired effects, phenols, color developing agents having one sulfonylurea group in the molecule, or conventional known color developing agents comprised of organic acids may be used together with the compound of formula (I) of the present invention. These conventional color developing agents include for example 2,2-bis(4-hydroxyphenyl)propane(bisphenol A), 1,1-bis(4-hydroxyphenyl)-1-phenylethane, 1,4-bis(1-methyl-1-(4'-hydroxyphenyl)ethyl)benzene, 1,3-bis(1-methyl-1-(4'-hydroxyphenyl)ethyl)benzene, dihydroxydiphenyl ether (Japanese Unexamined Patent Publication (Kokai) No. 1-180382), benzyl p-hydroxybenzoate (Japanese Unexamined Patent Publication (Kokai) No. 52-140483), bisphenol S, 4-hydroxy-4'-isopropyloxydiphenylsulfone (Japanese Unexamined Patent Publication (Kokai) No. 60-13852), 1,1-di(4-hydroxyphenyl)cyclohexane, 1,7-di(4-hydroxyphenylthio)-3,5-dioxaheptane (Japanese Unexamined Patent Publication (Kokai) No. 59-52694), 3,3'-diallyl-4,4'-dihydroxydiphenylsulfone (Japanese Unexamined Patent Publication (Kokai) No. 60-208286), 2,4-bis(phenylsulfonyl)phenol (Japanese Unexamined Patent Publication (Kokai) No. 8-269000) etc.

Further, as color developing agents other than phenol, Japanese Unexamined Patent Publication (Kokai) No. 5-32601 discloses, for example, N-(p-toluenesulfonyl)-N'-phenylurea, N-(p-toluenesulfonyl)-N'-(p-methoxyphenyl)urea, N-(p-toluenesulfonyl)-N'-(o-tolyl)urea, N-(p-toluenesulfonyl)-N'-(m-tolyl)urea, N-(p-toluenesulfonyl)-N'-(p-tolyl)urea, N-(p-toluenesulfonyl)-N'-(o-chlorophenyl)urea, N-(benzenesulfonyl)-N'-phenylurea, N-(p-chlorobenzenesulfonyl)-N'-phenylurea, etc.

Further, in the present invention, to an extent not impairing the effect of the present invention, it is also possible to use conventional known thermo-fusible substances (sensitizers). As examples of these, phenyl 1-hydroxy-2-naphthoate (Japanese Unexamined Patent Publication (Kokai) No. 57-191089), p-benzylphenyl (Japanese Unexamined Patent Publication (Kokai) No. 60-82382), benzylnaphthylether (Japanese Unexamined Patent Publication (Kokai) No. 58-87094), dibenzyl terephthalate (Japanese Unexamined Patent Publication (Kokai) No. 58-98285), benzyl p-benzyloxybenzoate (Japanese Unexamined Patent Publication (Kokai) No. 57-201691), diphenyl carbonate and ditolyl carbonate (Japanese Unexamined Patent Publication (Kokai) No. 58-136489), m-terphenyl (Japanese Unexamined Patent Publication (Kokai) No. 57-89994), 1,2-bis(m-tolyloxy)ethane (Japanese Unexamined Patent Publication (Kokai) No. 60-56588), 1,5-bis(p-methoxyphenoxy)-3-oxapentane (Japanese Unexamined Patent Publication (Kokai) No. 62-181183), diesters of oxalic acid (Japanese Unexamined Patent Publication (Kokai) No. 64-1583), 1,4-bis(p-tolyloxy)benzene (Japanese Unexamined Patent Publication (Kokai) No. 2-153783), etc. may be mentioned.

The thermosensitive colored image-forming layer of the thermosensitive recording material of the present invention optionally further contains waxes and preferably contains organic and inorganic pigments. The colored image-forming layer contains a binder for binding the components as mentioned above to the substrate.

In the thermosensitive colored image-forming layer, preferably, the color-forming leuco dye is contained in a content of 5 to 20% by mass based on the total dry mass of the colored image-forming layer. The content of the novel color-developing agent of the present invention is preferably generally 5 to 50 mass %. When the content of the color developing agent is less than 5 mass %, the color developing performance of the resultant colored image-forming layer may be insufficient, and when the content of the color developing agent is more than 50 mass %, the color developing performance of the resultant colored image-forming layer may be saturated and an economical disadvantage may occur. When the sensitizing agent is employed, and when the content of the sensitizing agent is less than 5 mass %, a satisfactory sensitizing effect on the colored image-forming layer may not be expected. Also, when the content of the sensitizing agent is more than 50% by mass, the sensitizing effect may be saturated and no further enhancement in the sensitivity of the colored image-forming layer may be expected.

Where the thermosensitive colored image-forming layer contains a conventional phenolic compound- or organic acid-containing color developing compound, the content of the conventional color-developing compound is preferably 5 to 40% by mass based on the total dry mass of the colored image-forming layer. When the sensitizing agent is contained, the content of the sensitizing agent is preferably 10 to 40% by mass based on the total dry mass of the colored image-forming layer. When the wax and the white pigments are contained, the contents of the wax and the white pigment are respectively 2 to 20% by mass and 2 to 50% by mass based on the total dry weight of the colored image-forming layer. Also, the binder is contained in a content of 5 to 20% by mass based on the total dry mass of the colored image-forming layer.

As the above organic or inorganic pigments, for example, calcium carbonate, silica, zinc oxide, titanium dioxide, aluminum hydroxide, zinc hydroxide, barium sulfate, clay, calcinated clay, talc, and surface-treated calcium carbonate, silica and other inorganic fine particulate powder, as well as urea-formaldehyde resin, styrene-methacrylate copolymer, and polystyrene resin and other organic fine particulate etc. may be mentioned.

As the wax, for example, paraffin, amide-waxes, bisimide waxes, higher fatty acid metal salt waxes, and other known ones may be used.

For the binder, water-soluble polymeric materials, for example, various polyvinyl alcohols different in molecular weight from each other, starch and derivatives thereof, for example, cellulose derivatives such as methoxycellulose, carboxymethylcellulose, methylcellulose and ethylcellulose, sodium salt of polyacrylic acid, polyvinyl pyrrolidone, acrylic acid amide-acrylate ester copolymers, acrylic acid amide-acrylate ester-methacrylic acid terpolymers, alkali salts of styrene-maleic anhydride copolymers, polyacrylamide, sodium alginate, gelatin, casein and the like; latices of polyvinyl acetate, polyurethanes, styrene-butadiene copolymers, poly acrylic acid, polyacrylate esters, vinyl chloride-vinyl acetate copolymers, polybutyl methacrylate, ethylene-vinyl acetate copolymers, and styrene-butadiene-acrylic monomer copolymers may be used.

The substrate sheet usable for the thermosensitive recording medium of the present invention may be selected from paper sheets (acid paper sheets and neutral paper sheets), coated paper sheets produced by coating paper sheets with a pigment and/or a latex, laminate paper sheets, synthetic paper sheets made from, for example, a polyolefin resin, and plastic films. The thermosensitive recording material is produced by coating at least one surface of the substrate sheet with a coating liquid containing the above-mentioned required components and drying the coating liquid layer on the substrate sheet. The amount of the coating liquid applied to the substrate sheet is controlled so that the resultant colored image-forming layer preferably has a dry mass of 1 to 15 g/m², more preferably 2 to 10 g/m².

In the thermosensitive recording material of the present invention, the thermosensitive colored image-forming layer is optionally coated with an uppercoat layer, for example, a protective layer or a printing layer. Also, optionally, an undercoat layer comprising a pigment, preferably an oil-absorbing pigment, and a binder, is formed between the substrate sheet layer and the thermosensitive colored image-forming layer.

EXAMPLES

The present invention will be further illustrated by the following examples. Unless indicated otherwise, the "parts" and "%" indicate "parts by mass" and "mass %" respectively.

Synthesis Example 1

1,5-(3-oxopentylene)bis(3-(3'-(p-toluenesulfonyl)ureido)benzoate)

(1) Synthesis of 1,5-(3-oxopentylene) bis(3-aminobenzoate)

A three-necked flask equipped with a thermometer, a reflux condenser and a dropping funnel, was charged with 9.84 g of 3-aminobenzoate and 120 ml of N,N-dimethylformamide (dehydrated). Into this solution, 9.96 g of potassium carbonate (anhydrous) was added. While agitating the mixture by a magnetic stirrer, 5.16 g of bis(2-chloroethyl)ether was added at room temperature. This reaction suspension was agitated at room temperature, then heated and refluxed at 130° C. for 4 hours, then cooled to room temperature. The reaction suspension was added to 300 ml of water and vigorously agitated, whereupon a white solid precipitated. By filtering this aqueous suspension, 10.5 g of 1,5-(3-oxopentylene) bis(3-aminobenzoate) was obtained as a white solid. The obtained white solid was confirmed to be the target substance by various types of analysis including DSC, NMR, and IR analysis.

(2) Synthesis of 1,5-(3-oxopentylene)bis(3-(3'-(p-toluenesulfonyl)ureido)benzoate)

A three necked flask equipped with a dropping funnel, a thermometer and a reflux condenser was charged with 10.5 g of 1,5-(3-oxopentylene)bis(3-aminobenzoate), and then with 200 ml of acetonitrile which were then agitated to dissolve. While agitating the mixture by a magnetic stirrer, 13.8 g of p-toluenesulfonyl isocyanate was added dropwise at room temperature from the dropping funnel. When continuing to agitate the reaction mixture, a large amount of white solid precipitated. The reaction mixture was heated at 80° C. for 4 hours, then cooled and filtered, whereby 19.5 g of white crystals was obtained.

The analysis results of the white crystals are shown below.

Melting point (by DSC): 139.8° C.

Results of NMR measurement (in DMSO) (figures are ppm)

δ=2.36(s, 6H), 3.77(t, 4H), 4.36(t, 4H), 7.32(t, 2H), 7.41(d, 4H), 7.52-7.54(m, 4H), 7.83(d, 4H), 7.98(t, 2H)

Other peaks, which were considered to be due to an N—H bond, appeared at about δ=9.07, 10.85.

Synthesis Example 2

1,5-pentamethylene bis(3-(3'-(p-toluenesulfonyl)ureido)benzoate (1) Synthesis of 1,5-pentamethylene bis(3-aminobenzoate)

A three-necked flask equipped with a thermometer, a reflux condenser and a dropping funnel, was charged with 8.20 g of 3-aminobenzoate and 100 ml of N,N-dimethylformamide (dehydrated). Into this solution, 8.30 g of potassium carbonate (anhydrous) was added. While agitating the mixture by a magnetic stirrer, 6.85 g of 1,5-dibromopentane was added at room temperature. This reaction suspension was agitated at room temperature, then heated and refluxed at 130° C. for 4 hours, then cooled to room temperature. The reaction suspension was added to 300 ml of water and vigorously agitated. This aqueous suspension was extracted by 150 ml of ethyl acetate and the solvent distilled off, whereupon 9.75 g of 1,5-pentamethylene bis(3-aminobenzoate) was obtained as an oily substance. The obtained oily substance was confirmed to be the target substance by various types of analysis including NMR, and IR analysis.

(2) Synthesis of 1,5-pentamethylene bis(3-(3'-(p-toluenesulfonyl)ureido)benzoate)

A three necked flask equipped with a dropping funnel, a thermometer and a reflux condenser was charged with 9.75 g of 1,5-pentamethylene bis(3-aminobenzoate), and then with 200 ml of acetonitrile which were then agitated to dissolve. While agitating the mixture by a magnetic stirrer, 12.7 g of p-toluenesulfonyl isocyanate was added dropwise at room temperature from the dropping funnel. When continuing to agitate the reaction mixture, a large amount of white solid precipitated. The reaction mixture was heated at 80° C. for 4 hours, then cooled and filtered, whereby 19.8 g of white crystals was obtained.

The analysis results of the white crystals are shown below.

Melting point: 116-124° C.

Results of NMR measurement (in DMSO) (figures are ppm)

δ=1.50(d, 2H), 1.74(t, 4H), 2.36(s, 6H), 4.26(t, 4H), 7.36(t, 4H), 7.40(d, 2H), 7.56(t, 4H), 7.84(d, 4H), 7.99(d, 2H)

Other peaks, which were considered to be due to an N—H bond, appeared at about δ=9.08, 10.74.

Synthesis Example 3

1,6-hexamethylene bis(3-(3'-(p-toluenesulfonyl)ureido)benzoate (1) Synthesis of 1,6-hexamethylene bis(3-aminobenzoate)

A three-necked flask equipped with a thermometer, a reflux condenser and a dropping funnel, was charged with 9.67 g of 3-aminobenzoate and 100 ml of N,N-dimethylformamide (dehydrated). Into this solution, 9.74 g of potassium carbonate (anhydrous) was added. While agitating the mixture by a magnetic stirrer, 8.61 g of 1,6-dibromohexane was added at room temperature. This reaction suspension was agitated at room temperature, then heated and refluxed at 130° C. for 4 hours, then cooled to room temperature. The reaction suspension was added to 300 ml of water and vigorously agitated. This aqueous suspension was extracted by 150 ml of ethyl acetate and the solvent distilled off, whereupon 10.7 g of 1,6-hexamethylene bis(3-aminobenzoate) was obtained as a white solid. The obtained white solid was confirmed to be the target substance by various types of analysis including DSC, NMR, and IR analysis.

(2) Synthesis of 1,6-hexamethylene bis(3-(3'-(p-toluenesulfonyl)ureido)benzoate)

A three necked flask equipped with a dropping funnel, a thermometer and a reflux condenser was charged with 10.70 g of 1,6-hexamethylene bis(3-aminobenzoate), and then with 200 ml of acetonitrile which were then agitated to dissolve. While agitating the mixture by a magnetic stirrer, 13.8 g of p-toluenesulfonyl isocyanate was added dropwise at room temperature from the dropping funnel. When continuing to agitate the reaction mixture, a large amount of white solid precipitated. The reaction mixture was heated at 80° C. for 4 hours, then cooled and filtered, whereby 20.24 g of white crystals was obtained.

The analysis results of the white crystals are shown below.

Melting point: 125° C.

Results of NMR measurement (in DMSO) (figures are ppm)

$\delta$=1.45(s, 4H), 1.72(s, 4H), 2.39(s, 6H), 4.26(t, 4H), 7.38(t, 4H), 7.43(d, 2H), 7.86(d, 4H), 8.02(d, 2H)

Other peaks, which were considered to be due to an N—H bond, appeared at about $\delta$=9.08, 10.78.

Synthesis Example 4

1,4-tetramethylene bis(3-(3'-(p-toluenesulfonyl)ureido)benzoate (1) Synthesis of 1,4-tetramethylene bis(3-aminobenzoate)

A three-necked flask equipped with a thermometer, a reflux condenser and a dropping funnel, was charged with 9.64 g of 3-aminobenzoate and 100 ml of N,N-dimethylformamide (dehydrated). Into this solution, 9.71 g of potassium carbonate (anhydrous) was added. While agitating the mixture by a magnetic stirrer, 7.60 g of 1,4-dibromobutane was added at room temperature. This reaction suspension was agitated at room temperature, then heated and refluxed at 130° C. for 4 hours, then cooled to room temperature. The reaction suspension was added to 300 ml of water and vigorously agitated. This aqueous suspension was extracted by 150 ml of ethyl acetate and the solvent distilled off, whereupon 9.60 g of 1,4-tetramethylene bis(3-aminobenzoate) was obtained as a white solid. The obtained white solid was confirmed to be the target substance by various types of analysis including DSC, NMR, and IR analysis.

(2) Synthesis of 1,4-tetramethylene bis(3-(3'-(p-toluenesulfonyl)ureido)benzoate)

A three necked flask equipped with a dropping funnel, a thermometer and a reflux condenser was charged with 9.60 g of 1,4-tetramethylene bis(3-aminobenzoate), and then with 200 ml of acetonitrile which were then agitated to dissolve. While agitating the mixture by a magnetic stirrer, 13.6 g of p-toluenesulfonyl isocyanate was added dropwise at room temperature from the dropping funnel. When continuing to agitate the reaction mixture, a large amount of white solid precipitated. The reaction mixture was heated at 80° C. for 4 hours, then cooled and filtered, whereby 20.1 g of white crystals was obtained.

The analysis results of the white crystals are shown below.

Melting point: 159° C.

Results of NMR measurement (in DMSO) (figures are ppm)

$\delta$=1.83(s, 4H), 2.38(s, 6H), 4.31(t, 4H), 7.39(d, 4H), 7.42(d, 2H), 7.57(t, 4H), 7.85(d, 4), 8.00(d, 2H)

Other peaks, which were considered to be due to an N—H bond, appeared at about $\delta$=9.07, 10.76.

Example 1

A thermosensitive recording sheet was prepared by the following procedures.

(1) Preparation of a Pigment-Coated Paper Sheet

A coating liquid was prepared by mixing an aqueous dispersion of 85 parts by mass of calcined clay (trademark: ANSILEX, made by ENGELHARD CORPORATION) in 320 parts by mass of water with 40 parts by mass of an aqueous emulsion of a styrene-butadiene copolymer having a solid content of 50% by mass and 50 parts by mass of a 10% aqueous oxidized starch solution. The coating liquid was coated in a dry solid amount of 7.0 g/m$^2$ on a paper sheet having a basis weight of 48 g/m$^2$ and dried. A pigment-coated paper sheet was obtained.

(2) Preparation of Dispersion A

| Component | Parts by mass |
| --- | --- |
| 3-(N,N-dibutylamino)-6-methyl-7-anilinofluoran | 20 |
| 10% aqueous polyvinyl alcohol | 10 |
| Water | 70 |

A mixture of the above-mentioned components was subjected to a pulverizing procedure using a sand grinder to such an extent that the average particle size of the dye precursor was 1 μm or less.

(3) Preparation of Dispersion B

| Component | Parts by mass |
| --- | --- |
| 1,5-(3-oxopentylene) bis(3-(3'-(p-toluenesulfonyl)ureido)benzoate) | 20 |
| 10% aqueous polyvinyl alcohol | 10 |
| Water | 70 |

A mixture of the above-mentioned components was subjected to a pulverizing procedure using a sand grinder to such an extent that the average particle size of the dye precursor was 1 μm or less.

(4) Preparation of Dispersion C

| Component | Parts by mass |
| --- | --- |
| Di-p-methylbenzyl oxalate | 20 |
| 10% aqueous polyvinyl alcohol | 10 |
| Water | 70 |

A mixture of the above-mentioned components was subjected to a pulverizing procedure using a sand grinder to such an extent that the average particle size of the dye precursor was 1 μm or less.

(5) Formation of Colored Image-Forming Layer

A coating liquid for a thermosensitive colored image-forming layer was prepared by mixing 60 parts by mass of the dispersion (A), 120 parts by mass of the dispersion (B) and 120 parts by mass of the dispersion (C) with 23 parts by mass of a kaolinite pigment (trademark: HG CLAY, made by HUBER CO.), 20 parts by mass of a 25% aqueous zinc stearate dispersion, 15 parts by mass of a 30% aqueous paraffin dispersion and 120 parts by mass of a 10% aqueous polyvinyl alcohol solution, and then stirring the mixture. The coating liquid was coated on a surface of the pigment-coated paper sheet and dried to form a thermosensitive colored image-forming layer having a dry solid amount of 5.0 g/m$^2$ on the pigment-coated paper sheet, thereby a thermosensitive recording sheet was obtained.

(6) Super Calender Treatment

The thermosensitive recording sheet was subjected to a supper calender treatment, to form a smoothed surface with a smoothness of 800 to 1000 seconds.

(7) Tests

The smoothed thermosensitive recording sheet was subjected to the following tests.

(a) Whiteness

The whiteness of a sample of the thermosensitive recording sheet was measured by a HUNTER whiteness meter (made by TOYO SEIKI SEISAKUSHO).

(b) Color-Forming Test

A sample of the thermosensitive recording sheet was printed in a checkered pattern by using a dynamic thermosensitive color-forming simulator (Model: THPMD, made by OKURA DENKI K.K.) under a printing voltage of 21.7 volts at pulse widths of 0.7 ms and 1.0 ms. The color density of the resultant colored images was measured by a Macbeth reflection color density tester (model: RD-914). The measured color density value represents a recording sensitivity of the recording sheet.

(c) Test for Resistance of Non-Printed Portion of Recording-Sheet to Spontaneous Color Formation Under High Humidity Condition A sample of the thermosensitive recording sheet was stored in a vessel at a temperature of 40° C. at a relative humidity of 90% for 24 hours. Then the color density of the sample was measured by the same procedure as in test (b).

(d) Test for Resistance of Non-Printed Portion of Recording-Sheet to Spontaneous Color Formation Under High Temperature Condition A sample of the thermosensitive recording sheet was stored in a vessel at a temperature of 60° C. for 24 hours. Then the color density of the sample was measured by the same procedure as in test (b).

Example 2

The same procedure as followed as in Example 1. Provided, however, that in the preparation of the dispersion B, instead of 1,5-(3-oxopentylene) bis(3-(3'-(p-toluenesulfonyl)ureido)benzoate), 1,5-pentamethylene bis(3-(3'-(p-toluenesulfonyl)ureido)benzoate) was used. The test results are shown in Table 1.

Example 3

The same procedure as followed as in Example 1. Provided, however, that in the preparation of the dispersion B, instead of 1,5-(3-oxopentylene) bis(3-(3'-(p-toluenesulfonyl)ureido)benzoate), 1,3-trimethylene bis(3-(3'-(p-toluenesulfonyl)ureido)benzoate) was used. The test results are shown in Table 1.

Example 4

The same procedure as followed as in Example 1. Provided, however, that in the preparation of the dispersion B, instead of 1,5-(3-oxopentylene) bis(3-(3'-(p-toluenesulfonyl)ureido)benzoate), 1,8-(3,6-dioxaoctylene) bis(3-(3'-(p-toluenesulfonyl)ureido)benzoate) was used. The test results are shown in Table 1.

Example 5

The same procedure as followed as in Example 1. Provided, however, that in the preparation of the dispersion B, instead of 1,5-(3-oxopentylene) bis(3-(3'-(p-toluenesulfonyl)ureido)benzoate), 1,6-hexamethylene bis(3-(3'-(p-toluenesulfonyl)ureido)benzoate) was used. The test results are shown in Table 1.

Example 6

The same procedure as followed as in Example 1. Provided, however, that in the preparation of the dispersion B, instead of 1,5-(3-oxopentylene) bis(3-(3'-(p-toluenesulfonyl)ureido)benzoate), 1,4-tetramethylene bis(3-(3'-(p-toluenesulfonyl)ureido)benzoate) was used. The test results are shown in Table 1.

Comparative Example 1

The same procedure as followed as in Example 1. Provided, however, that in the preparation of the dispersion B, instead of 1,5-(3-oxopentylene) bis(3-(3'-(p-toluenesulfonyl)ureido)benzoate, 2,2-bis(4-hydroxyphenyl)propane (bisphenol A) was used. The test results are shown in Table 1.

TABLE 1

| | Whiteness (D) | 0.7 ms color density (D) | 1.0 ms color density (D) | Non-printed part density (D) | Nonprinted part density (D) after humidity resistance test | Non-printed part density (D) after heat resistance test |
|---|---|---|---|---|---|---|
| Ex. 1 | 81.0 | 0.80 | 1.38 | 0.06 | 0.06 | 0.08 |
| Ex. 2 | 80.7 | 0.76 | 1.35 | 0.07 | 0.07 | 0.07 |
| Ex. 3 | 80.9 | 0.75 | 1.33 | 0.07 | 0.07 | 0.09 |
| Ex. 4 | 80.6 | 0.76 | 1.34 | 0.07 | 0.07 | 0.07 |
| Ex. 5 | 80.3 | 0.93 | 1.39 | 0.07 | 0.08 | 0.09 |
| Ex. 6 | 80.8 | 0.80 | 1.34 | 0.07 | 0.06 | 0.07 |
| Comp. Ex. 1 | 78.0 | 0.75 | 1.36 | 0.07 | 0.14 | 0.13 |

Table 1 clearly shows that the thermosensitive recording material of the present invention exhibited a high whiteness and a high color developing performance, the non-printed portion of the material showed a high and that resistance to spontaneous color formation under high temperature and high humidity conditions, thereby it exhibited superior thermosensitive performance.

Example 7

A thermosensitive recording sheet was prepared by the following procedure:

(1) Preparation of Pigment-Coated Paper Sheet

A pigment-coated paper sheet was prepared by the same method as in Example 1 (1).

(2) Preparation of Dispersion A

| Component | Parts by mass |
|---|---|
| 3-(N,N-dipentylamino)-6-methyl-7-anilinofluoran | 10 |
| Di-p-methylbenzyl oxalate | 8 |
| Di-p-chlorobenzyl oxalate | 2 |
| 10% aqueous polyvinyl alcohol | 10 |
| Water | 70 |

A mixture of the above-mentioned components was subjected to a pulverizing procedure using a sand grinder to such an extent that the average particle size of the dye precursor was 1 μm or less.

(3) Preparation of Dispersion B

| Component | Parts by mass |
|---|---|
| 1,5-(3-oxopentylene) bis(3-(3'-(p-toluenesulfonyl)ureido)benzoate) | 20 |
| 10% aqueous polyvinyl alcohol | 10 |
| Water | 70 |

A mixture of the above-mentioned components were subjected to a pulverizing procedure using a sand grinder to such an extent that the average particle size of the color-developing agent was 1 μm or less.

(4) Formation of Colored Image Forming Layer

A coating liquid for a thermosensitive colored image-forming layer was prepared by mixing 20 parts by mass of the dispersion (A) and 30 parts by mass of the dispersion (B) with 40 parts by mass of a 50% kaolinite pigment (trademark: HG CLAY, made by HUBER CO.), 3 parts by mass of a 35% aqueous zinc stearate dispersion, and 8 parts by mass of a 10% aqueous polyvinyl alcohol solution, and then stirring the mixture. The coating liquid was coated on a surface of the pigment-coated paper sheet and dried to form a thermosensitive colored image-forming layer having a dry solid amount of 5.0 g/m$^2$ on the pigment-coated paper sheet.

(5) Super Calender Treatment

The thermosensitive recording sheet was subjected to a supper calender treatment, to form a smoothed surface with a smoothness of 800 to 1000 seconds.

(6) Tests (e) Test for Resistance of Non-Printed Portion of Recording-Sheet to Spontaneous Color Formation Under High Temperature Condition A sample of the thermosensitive recording sheet was printed in a checkered pattern by using a dynamic thermosensitive color-forming simulator (Model: THPMD, made by OKURA DENKI K.K.) under a printing voltage of 21.7 volts at a pulse width of 1.0 ms, then was stored in a vessel at a temperature of 100° C. for 1 hour. The color density of the resultant colored images was measured by a Macbeth reflection color density tester (model: RD-914).

(f) Plasticizer Resistance Test

A sample of the thermosensitive recording sheet printed at a pulse width of 1.0 ms in the same manner as in the (e) Test for Resistance of Non-Printed Portion of Recording-sheet to Spontaneous Color Formation Under High Temperature Condition was sandwiched between the poly vinyl chloride films (brand name: Hiwrap KMA-W, made by Mitsui Chemical, poly vinyl chloride film belonging to a group with the greatest content of plasticizers among packaging-used plastic film), given a load of 10 gf/cm$^2$, and then was allowed to stand in a 40° C. thermostat for 17 hours. The poly vinyl chloride films were then peeled off and the residual image color density was measured by a Macbeth reflection color density tester. The retention rate of the image was calculated in accordance with the following equation.

Image retention rate (%)=(density after plasticizer resistance test/original density)×100

The results of the (e) Test for Resistance of Non-Printed Portion of Recording-sheet to Spontaneous Color Formation Under High Temperature Condition and (f) Plasticizer Resistance Test are shown in Table 2.

Example 8

The same procedure as followed as in Example 7. Provided, however, that in the preparation of the dispersion B, instead of 1,5-(3-oxopentylene) bis(3-(3'-(p-toluenesulfonyl)ureido)benzoate), 1,5-pentamethylene bis(3-(3'-(p-toluenesulfonyl)ureido)benzoate) was used. The test results are shown in Table 2.

Example 9

The same procedure as followed as in Example 7. Provided, however, that in the preparation of the dispersion B, instead of 1,5-(3-oxopentylene) bis(3-(3'-(p-toluenesulfonyl)ureido)benzoate), 1,3-trimethylene bis(3-(3'-(p-toluenesulfonyl)ureido)benzoate) was used. The test results are shown in Table 2.

Example 10

The same procedure as followed as in Example 7. Provided, however, that in the preparation of the dispersion B, instead of 1,5-(3-oxopentylene) bis(3-(3'-(p-toluenesulfonyl)ureido)benzoate), 1,8-(3,6-dioxaoctylene) bis(3-(3'-(p-toluenesulfonyl)ureido)benzoate) was used. The test results are shown in Table 2.

Example 11

The same procedure as followed as in Example 7. Provided, however, that in the preparation of the dispersion B, instead of 1,5-(3-oxopentylene) bis(3-(3'-(p-toluenesulfonyl)ureido)benzoate), 1,6-hexamethylene bis(3-(3'-(p-toluenesulfonyl)ureido)benzoate) was used. The test results are shown in Table 2.

Example 12

The same procedure as followed as in Example 7. Provided, however, that in the preparation of the dispersion B, instead of 1,5-(3-oxopentylene) bis(3-(3'-(p-toluenesulfonyl)ureido)benzoate), 1,4-tetramethylene bis(3-(3'-(p-toluenesulfonyl)ureido)benzoate) was used. The test results are shown in Table 2.

Comparative Example 2

The same procedure as followed as in Example 7. Provided, however, that in the preparation of the dispersion B, instead of 1,5-(3-oxopentylene) bis(3-(3'-(p-toluenesulfonyl)ureido)benzoate, 2,2-bis(4-hydroxyphenyl)propane (bisphenol A) was used. The test results are shown in Table 2.

TABLE 2

| | High heat resistance test | | | |
|---|---|---|---|---|
| | 1.0 ms color density (D) | Nonprinted part density (D) | Post-test nonprinted part density (D) | Retention rate (%) in PVC film test |
| Ex. 7 | 1.43 | 0.06 | 0.30 | 95 |
| Ex. 8 | 1.42 | 0.07 | 0.35 | 90 |
| Ex. 9 | 1.40 | 0.07 | 0.45 | 78 |
| Ex. 10 | 1.41 | 0.07 | 0.48 | 79 |
| Ex. 11 | 1.45 | 0.07 | 0.48 | 98 |
| Ex. 12 | 1.40 | 0.06 | 0.31 | 80 |
| Comp. Ex. 2 | 1.40 | 0.07 | 1.13 | 18 |

As shown in Table 2, in a high humidity environment corresponding to the inside of a motor vehicle in hot summer weather, Comparative Example 2 exhibits vigorous color development making discrimination of the recorded image impossible, while Examples 7, 8, 9, 10, 11 and 12 using the color-developing agent of the present invention enabled the recorded image to be read well. Further, Comparative Example 2 suffered from loss of color of the recorded image and therefore inability of reading when contacting PVC wrapping film, while Examples 7, 8, 9, 10, 11 and 12 using the color developing agent of the present invention held the recorded image and enabled it to be discriminated well.

The present invention provides thermosensitive recording materials having a high whiteness, an excellent colored image-retaining stability due to which the color-developed images are not erased, and a high recording sensitivity. The thermosensitive recording materials of the present invention exhibit a good storage property over a long time, have heat resistance of the recorded images, in particular a high environmental resistance such as a high heat resistance and humidity resistance under high temperature conditions such as envisioned in motor vehicles in hot summer weather or due to heating by a microwave oven, a high oil resistance, and a high plasticizer resistance, and have a high recording sensitivity and whiteness. Thus the thermosensitive recording materials of the present invention are usable for cash-dispenser sheets, traveller's tickets, parking lot tickets, entry tickets, commuter passes, labels, for example, POS labels, cards, for example, prepaid cards, etc.

While the invention has been described with reference to specific embodiments chosen for purpose of illustration, it should be apparent that numerous modifications could be made thereto by those skilled in the art without departing from the basic concept and scope of the invention.

The invention claimed is:

1. A thermosensitive recording material comprising a substrate sheet and a thermosensitive colored image-forming layer formed on at least one surface of the substrate sheet and comprising at least one colorless or light-colored dye precursor and a color-developing agent reactive with the dye precursor upon heating to thereby develop a color, wherein the color developing agent comprises at least one compound of the formula (I):

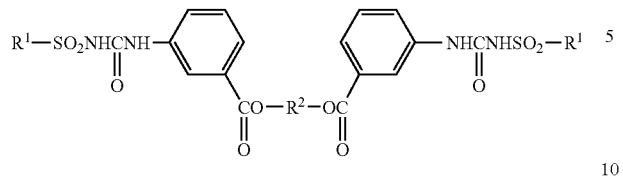

(I)

wherein R¹ represents a member selected from the group consisting of unsubstituted aromatic hydrocarbon groups and substituted aromatic hydrocarbon groups with at least one substituent selected from the group consisting of a methyl group and a chlorine atom, and R² represents a divalent organic group.

2. The thermosensitive recording material as claimed in claim 1, wherein in the formula (I), the divalent organic group represented by R² is selected from the group consisting of —(CH₂)$_m$— groups, and —(CH₂CH₂O)$_n$—CH₂CH₂— groups
wherein m represents an integer of 1 to 30, and n represents an integer of 1 to 20.

3. 1,5-(3-oxopentylene) bis(3-(3'-(p-toluenesulfonyl)ureido)benzoate) of the following chemical formula (II):

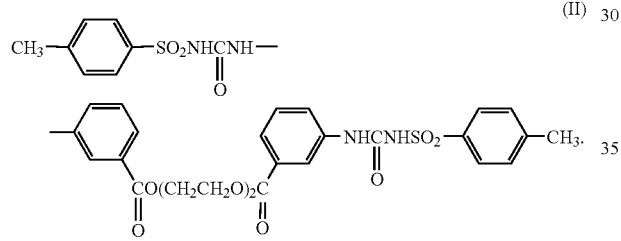

(II)

4. 1,5-pentamethylene bis(3-(3'-(p-toluenesulfonyl)ureido)benzoate) of the following chemical formula (III):

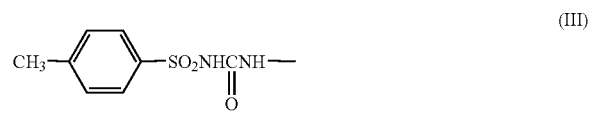

(III)

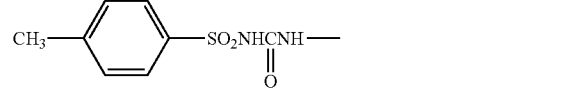

5. 1,6-hexamethylene bis(3-(3'-(p-toluenesulfonyl)ureido)benzoate) of the following chemical formula (IV):

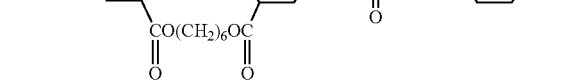

(IV)

* * * * *